United States Patent [19]

Thottathil

[11] Patent Number: 4,851,514

[45] Date of Patent: Jul. 25, 1989

[54] PROCESS FOR PREPARING A COMPOUND USEFUL IN PREPARING ACE INHIBITORS AND INTERMEDIATE PRODUCED THEREBY

[75] Inventor: John K. Thottathil, Lawrenceville, N.J.

[73] Assignee: E. R. Squibb & Sons, Inc., Princeton, N.J.

[21] Appl. No.: 92,360

[22] Filed: Sep. 2, 1987

Related U.S. Application Data

[62] Division of Ser. No. 44,691, May 1, 1987, Pat. No. 4,734,508.

[51] Int. Cl.$^4$ ............................ C07F 5/00; B01J 31/00
[52] U.S. Cl. ....................................... 534/15; 502/152
[58] Field of Search ............................................ 534/15

[56] References Cited

U.S. PATENT DOCUMENTS

| | | | |
|---|---|---|---|
| 4,337,201 | 6/1982 | Petrillo | 424/274 |
| 4,492,655 | 1/1985 | Gradeff et al. | 534/15 |
| 4,588,819 | 5/1986 | Thottathil | 548/532 |

OTHER PUBLICATIONS

H. Schumann et al., *Organometallics*, 3, 69 (1984).
P. N. Hazin et al., *Organometallics*, 6, 913 (1987).
Hart, F. A. and Saran, M. S., *J. Chem. Soc. Chem. Commun.*, 1968, 1614 [in Chem. Abst., vol. 70, 47567 (1969)].
"Organocerium Reagents, Nucleophilic Addition to Easily Enolizable Ketones", Imamoto et al., Tetrahedron Letters, vol. 25, No. 38, pp. 4233–4236, 1984.
"Cerium Chloride-Promoted Nucleophilic Addition of Grignard Reagents to Ketones An Efficient Method for the Synthesis of Tertiary Alcohols", Tetrahedron Letters, vol. 26, No. 39, pp. 4763–4766, 1985.

*Primary Examiner*—Brooks H. Hunt
*Assistant Examiner*—Virginia B. Caress
*Attorney, Agent, or Firm*—Burton Rodney

[57] ABSTRACT

A compound (for preparing an ACE inhibitor), namely, triphenyl cerium and a process for preparing same by reacting cerium trichloride ($CeCl_3$) with phenyllithium, are provided.

6 Claims, No Drawings

PROCESS FOR PREPARING A COMPOUND USEFUL IN PREPARING ACE INHIBITORS AND INTERMEDIATE PRODUCED THEREBY

This is a division of application Ser. No. 44,691, filed May, 1987, now U.S. Pat. No. 4,734,508.

FIELD OF THE INVENTION

The present invention relates to a process for preparing (cis)-4-hydroxy-4-phenyl-L-proline derivatives which are novel intermediates in the preparation of trans-4-substituted-L-prolines and, which in turn, are useful as intermediates in the preparation of certain angiotensin-converting enzyme (ACE) inhibitors.

DESCRIPTION OF THE INVENTION

In accordance with the present invention, a process is provided for preparing (cis)-4-hydroxy-4-phenyl-L-proline derivatives of the structure I

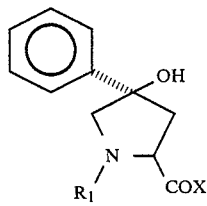

wherein $R_1$ is a nitrogen protecting group such as benzoyl, benzyloxycarbonyl, t-butoxycarbonyl, benzene sulfonyl, toluene sulfonyl, benzyl, benzhydryl, trityl, acetyl, trifluoroacetyl and the like, and X is $OR_2$ where $R_2$ is hydrogen or an acid protecting group such as lower alkyl, phenyl-lower alkyl or a metal ion such as Na, K or Li, or X is $NR_3R_4$ wherein $R_3$ and $R_4$ may be the same or different and are hydrogen, lower alkyl, aryl or arylalkyl or $R_3$ and $R_4$ together with the N to which they are attached form a 5-, 6- or 7-membered ring such as

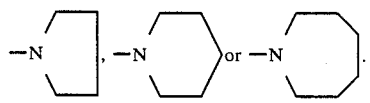

The process of the invention includes the step of reacting triphenylcerium

with the 4-ketoproline derivative III

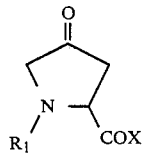

in the presence of an inert organic solvent such as tetrahydrofuran, ether, toluene or dioxane or a mixture of two or more thereof, at reduced temperatures of from about $-90°$ C. to about $-10°$ C. and preferably from about $-80°$ C. to about $-50°$ C., for a period of from about 0.5 to about 6 hours and preferably from about 0.5 to about 2 hours to form the proline derivative I.

In carrying out the above invention, the keto compound III will be employed in a molar ratio to the triphenylcerium compound II as set out below

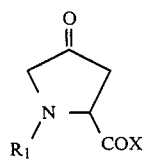

where in keto compound III, X is OH, then III is employed in a molar ratio to II of within the range of from about 2.5:1 to about 1:1 and preferably from about 2.2:1 to about 1.2:1; where in keto compound III, X is Oalkyl, then III is employed in a molar ratio to II of within the range of from about 4:1 to about 2:1 and preferably from about 3.5:1 to about 2.5:1, where in keto compound III, X is

then III is employed in a molar ratio to II of within the range of from about 4:1 to about 2:1 and preferably from about 3.5:1 to about 2.5:1; where in keto compound III, X is $NR_3R_4$, then III is employed in a molar ratio to II of within the range of from about 2.5:1 to about 1:1 and preferably from about 2.2:1 to about 1.2:1; and where in compound III, X is Ometal ion such as ONa, then III is employed in a molar ratio to II of within the range of from about 4:1 to about 2:1 and preferably from about 3.5:1 to about 2.5:1.

The (cis)-4-hydroxy-4-phenyl proline derivative I may then be employed to form a (trans)-4-phenyl-L-proline derivatives IV of the structure

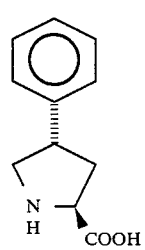

by treating the (cis)-4-hydroxy-4-phenyl proline derivatives I with a dehydrating agent such as p-toluenesulfonic acid in the presence of acetic anhydride, or any other dehydrating agent such as TFA (trifluoroacetic acid), $BF_3O(Et)_2$ (boron trifluoride etherate), methane sulfonyl chloride and triethylamine or refluxing with p-toluenesulfonic acid in an inert solvent such as methylene chloride, chloroform, toluene or tetrahydrofuran, employing a molar ratio of proline I:dehydrating agent of within the range of from about 0.1:1 to about 10:1, to form the protected compound acid

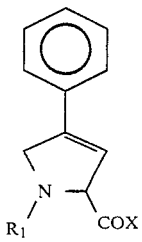

V which is treated with reducing agent such as an alkali or alkaline earth metal such as lithium, potassium, sodium, calcium and the like and ammonia employing a molar ratio of V:reducing agent of within the range of from about 0.25:1 to about 0.07:1 and preferably from about 0.2:1 to about 0.1:1, in the presence of an inert organic solvent such as tetrahydrofuran, to reduce the double bond and to remove the nitrogen protecting group and/or acid protecting group (if present) to form the acid IV. Where an acid protecting group X is also present then additional reducing agent will be employed to provide a molar ratio of V:reducing agent of within the range of from about 0.25:1 to about 0.1:1, and preferably from about 0.2:1 to about 0.15:1.

The phenyl proline derivative IV may be employed to form the corresponding trans-4-cyclohexyl-L-proline of the structure

VI

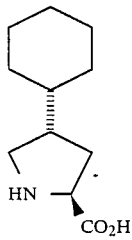

by reducing compound IV using, for example, hydrogen in the presence of a catalyst such as platinum, rhodium or other reducing catalyst.

In another embodiment, compounds of the formula VI can be directly prepared from compounds of the formula V as follows. Compound V is exhaustively reduced by treatment with an alkali or alkaline earth metal such as lithium, potassium, sodium, calcium and the like in the presence of an alcohol solvent such as ethanol or methanol, in liquid ammonia, to produce a compound of the formula VII

VIII

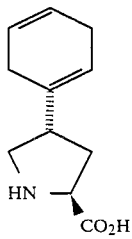

which is converted to compound VI by catalytic hydrogenation methods such as hydrogenating VII in the presence of a catalyst such as palladium, rhodium or other hydrogenation catatlyst.

The 4-substituted proline derivative IV may be employed to form angiotensin converting enzyme inhibitors as described in U.S. Pat. No. 4,337,201 to Petrillo.

The above Petrillo patent covers the following antiotensin-converting enzyme inhibitor which is also referred to as fosinopril.

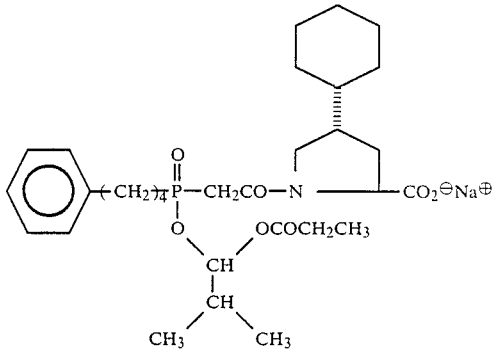

Listed below are definitions of the terms used in this specification. These definitions apply to the terms as they are used throughout the specification (unless they are otherwise limited in specific instances), either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to groups having 3 to 7 carbon atoms.

The term "aryl" refers to phenyl or phenyl substituted with halogen, alkyl, alkoxy, alkylthio, hydroxy, alkanoyl, nitro, amino, dialkylamino, or trifluoromethyl groups.

The term "alkanoyl" refers to groups having 2 to 9 carbon atoms.

The term "halogen" refers to fluorine, chlorine, bromine and iodine.

The 4-ketoproline derivatives III are known compounds and may be prepared as described by Patchett et al, "Studies on Hydroxyproline", J.A.C.S. 79, 185 (1957) and by Mauger et al, Chem. Rev. 66, 47 (1966).

The triphenylcerium compound II is a novel compound and may be prepared by reacting a solution of cerium trichloride CeCl₃ A in an inert organic solvent such as hexane, ether, tetrahydrofuran, toluene or a mixture of two or more thereof, with a solution of phenyllithium C₆H₅Li B in an inert organic solvent such as hexane, ether, tetrahydrofuran, toluene or the like, at a temperature within the range of from about −90° C. to about −10° C. and preferably from about −80 to about −50° C., for a period of from about 0.1 to about 3 hours and preferably from about 0.2 to about 1 hour, employing a molar ratio of A:B of within the range of from about 0.2:1 to about 1:1 and preferably from about 0.25:1 to about 0.35:1.

Examples of 4-keto proline derivatives III useful as starting materials in carrying out the process of the invention include, but are not limited to, the following.

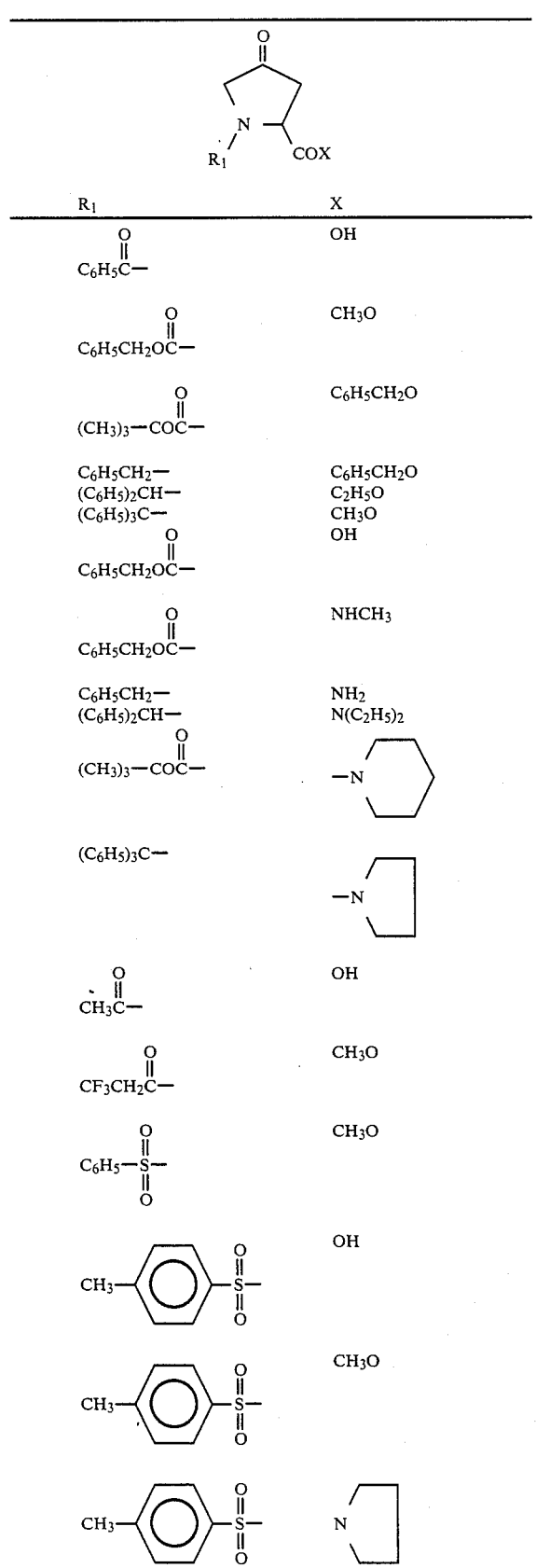

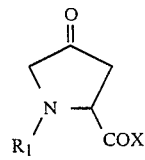

| $R_1$ | X |
|---|---|
| $C_6H_5-S(=O)(=O)-$ | OH |

The following working Examples represent preferred embodiments of the present invention. Unless otherwise indicated, all temperatures are expressed in degrees Centigrade.

EXAMPLE 1

Triphenylcerium

A 4-necked 500 ml flask was equipped with a mechanical stirrer, argon inlet, low temperature (−78° C.) thermometer and a septem cap. 250 ml dried tetrahydrofuran was added to the flask. 34.4 g (0.14 mol) anhydrous $CeCl_3$ was added to the tetrahydrofuran with vigorous stirring and stirring was continued for 2 hours at room temperature. A yellowish orange suspension formed which was cooled to −78° C. Phenyllithium (197.7 ml, 0.38 mol) in hexane-ether was added via a syringe through the spetum cap with vigorous stirring while the internal temperature was maintained at about −70° C. The initial yellow suspension changed color to white, then yellow, then orange and finally to a red solution. The red solution which was stirred for 30 minutes at −75° C. contained title compound and was employed as a reactant in Example 2.

EXAMPLE 2

(cis)-4-Hydroxy-4-phenyl-1-[(phenylmethoxy)-carbonyl]-L-proline

A 4-necked 1 liter flask was equipped with a mechanical stirrer, argon inlet, low temperature (−78° C.) thermometer and a septum cap. 200 ml dried tetrahydrofuran was added to the flask. Thereafter, 4-keto-1[(phenylmethoxy)carbonyl]-L-proline (50.0 g, 0.19 mol) was added to the tetrahydrofuran, the mixture was stirred to dissolve solids, and was cooled to −78° C. The red solution of triphenylcerium prepared in Example 1 was added via a double ended needle with vigorous stirring while maintaining the internal temperature at −70° C. The solution was stirred for 5 minutes at −78° C. while checking the TLC for complete reaction. 50 ml hydrochloric acid (1:1 conc. acid:water) was added with vigorous stirring and most of (not all) of the tetrahydrofuran was removed on a rotavap at ~40° C. The remaining concentrate was diluted with water, if necessary pH was adjusted to 1 with HCl, and the mixture extracted with ethyl acetate (3×200 ml). The combined organic phase was washed with HCl (1×100 ml, 1:1) and water (1×200 ml). The organic phase was extracted with saturated sodium bicarbonate solution (5×100 ml) and the combined sodium bicarbonate solution was back extracted once with ethyl acetate. The sodium bicarbonate solution was diluted with 250 ml ethyl acetate and acidified with vigorous stirring using concentrated hydrochloric acid. The layers were separated, the aqueous phase was extracted with ethyl acetate (3×200 ml), the combined organic phase washed with saturated sodium bisulfite solution (2×100 ml), the organic phase washed with water and brine, and dried over anhydrous MgSO$_4$, and the solvent evaporated on a rotavap to give a thick gum residue. The residue was dissolved in 40 ml ethyl acetate and the mixture was diluted with 50 ml hexane to a slight turbidity at room temperature and then seeded with crystals. After a few hours, the mixture was kept in a cold room overnight, filtered, washed with 30% ethyl acetate in hexane (ice-cold) and with hexane. The solids were air dried to give 46.7 g of title compound, m.p. 122°–126° C. $\alpha_D = -50°$ (c=1, CHCl$_3$).

EXAMPLE 3

4-Phenyl-1-[(phenylmethoxy)carbonyl]-3,4-dehydro-L-proline

The Example 2 proline compound (1 g, 0.003 mol) was combined with p-toluenesulfonic acid (0.56 g, 0.003 mol), in methylene chloride (20 ml) and the mixture was stirred for 5 minutes. Acetic anhydride (0.34 g, 0.0033 mol, 0.32 ml) was added and the mixture was stirred for 1 hour at room temperature to form a clear to slightly yellow solution. TLC showed that the reaction was almost complete. An additional 0.1 ml acetic anhydride was added and the reaction was allowed to proceed an additional 1 hour. TLC showed that the reaction was complete.

The methylene chloride was evaporated, the residue was reconstituted with ethyl acetate, washed with brine 5 times, dried (MgSO$_4$), filtered and evaporated to give 930 mg crude solid. The solid was recrystallized from ethyl acetate/hexane to yield 0.772 g, 79.6%, m.p. 154°–155° C.

EXAMPLE 4

(trans)-4-Phenyl-L-proline

Example 3 acid compound (20 g, 0.062 mol) in 40 ml tetrahydrofuran was added to a solution of lithium (3.03 g, 0.433 mol, 7 eq) and ammonia (2.5 l) (with 30 minutes of stirring) and tetrahydrofuran (2 l). After the addition, the reaction mixture was stirred for 40 minutes at −78° C. and quenched with ammonium chloride. Ammonia was evaporated at room temperature overnight. Tetrahydrofuran was evaporated, the solid residue was suspended in water and acidified with HCl to pH 1. The mixture was concentrated to 250 ml during which time some crystals formed. The pH was brought to 6.3 by addition of NaOH and left at room temperature overnight. The mixture was filtered, washed with water (2×50 ml, ice cold) and acetonitrile (2×150 ml) and hexane, air dried overnight to yield 11.8 g (100%) of title product. HPLC: cis-6.1%, trans 93.9%, ratio 15.4:1

Analyses: C$_{11}$H$_{13}$O$_2$N
Calcd: C, 69.01; H, 6.85; N, 7.33.
KF 6.5% H$_2$O, 0.74 moles: C, 64.50, H, 7.13: N, 6.85
Found: C, 64.69; H, 6.95; N, 7.29
$[\alpha]_D = +19.7°$ (c=1, 1N HCl)

EXAMPLE 5

(cis)-4-Hydroxy-4-phenyl-1-[(phenylmethoxy)carbonyl]-L-pyroline-pyrrolidine amide

A.

4-Keto-1-[(phenylmethoxy)carbonyl]carbonyl]-L-proline pyrrolidine amide

To a solution of 10 g (0.0377 mol) of 4-keto-1-[(phenylmethoxy)carbonyl]-L-proline in 200 ml methylene chloride was added 6.35 g (0.0415 mol) hydroxybenzotriazole. The mixture was cooled to 0° C., dicyclohexylcarbodiimide (87 g) added and the mixture was stirred at room temperature for 2 hours. The mixture was cooled to 0° C. and pyrrolidine (3.2 ml) added. The cooling bath was removed and the mixture was stirred at room temperature for 12 hours. The mixture was then cooled in an ice bath, acidified with 20% HCl to pH 2, filtered, washed with NaHCO$_3$ and HCl. Normal workup produced the title compound which was crystallized from ethyl acetate-hexane to yield 9.5 g, m.p. 109°–111° C.

B.

(cis)-4-Hydroxy-4-phenyl-1-[(phenylmethoxy)carbonyl]-L-prolinepyrrolidine amide

Triphenylcerium prepared as in Example 1 [from 12.87 g of CeCl$_3$ and 49 ml of PhLi]was added to a solution of the Part A keto-amide [30.0 g in 150 ml THF]with vigorous stirring at ~ −75° C. After the reaction, usual work up followed by crystallization produced the title compound in 78% (29.0 g) yield, m.p. 136°–138° C.

EXAMPLE 6

4-Phenyl-1-[(phenylmethoxy)carbonyl]-3,4-dehydro-L-proline pyrrolidine amide

Following the procedure of Example 3, except substituting the proline compound of Example 5B for the proline compound of Example 2, the title compound was obtained.

EXAMPLE 7

(cis)-4-Hydroxy-4-phenyl-1-[(phenylmethoxy)carbonyl]-L-proline benzyl ester

A. 4-Keto-1-[(phenylmethoxy)carbonyl]-L-proline benzyl ester 5 g (0.02 mmol) of 4-keto-1-[(phenylmethoxy)carbonyl]-L-proline was dissolved in 50 ml dimethylformamide, 2.62 ml (0.022 mmol) of benzyl bromide and 3.59 g (0.026 mmol) of potassium carbonate were added. The reaction mixture was stirred for 1 hour followed by normal extractive work to give the title compound, 3.5 gm (49% yield), m.p. 55°–56° C.
$[\alpha]_D = -6°$ (c=1, CHCl$_3$)

B.

(cis)-4-Hydroxy-4-phenyl-1-[(phenylmethoxy)carbonyl)]-L-proline benzyl ester

Triphenyl cerium prepared as in Example 1 [from 3.1 g of CelCl$_3$ and 11.78 ml of phenyllithium] was added to a solution of the Part A keto-ester (8.0 g in 40 ml THF] with vigorous stirring and cooling (−78° C.). After this addition, the reaction was quenched with 25% HCl acid and followed by usual extractive workup and crystallization to give the title compound in 77.8% (7.6 gm) yield.

EXAMPLE 8

(cis)-4-Hydroxy-4-phenyl-1-(benzoyl)-L-proline

Triphenylcerium prepared as in Example 1 [from 23.4 g $CeCl_3$ and 102 ml phenyllithium] was added to a solution of the keto acid (20 g in 140 ml THF) with vigorous stirring and cooling. After the addition, the reaction was stirred from 30 minutes at −78° C., quenched with 25% HCl acid and work up as usual to get the crude material which was crystallized from ethyl acetate to produce 17.0 g (64%) of the title material as white crystals.

EXAMPLE 9

4-phenyl-1-(benzoyl)-3,4-dehydro-L-proline

Following the procedure as described in Example 3 except substituting the Example 8 proline compound for the Example 2 proline compound, the title compound was obtained.

Example 10

(trans)-4-Phenyl-L-proline

The procedure of Example 4 was followed except that the Example 9 compound was used as the starting material. Thus, a solution of 2.0 g (0.0068 moles) of the dehydro-proline in 25 ml THF was added to a solution of lithium (0.33 g, 0.478 moles) in ammonia (300 ml) and THF (200 ml) at ∼−78° C. After the addition, the reaction mixture was stirred for 20 minutes at −78° C., quenched with 2.0 g ammonium chloride and worked up as in Example 4. (trans)-4-Phenyl-L-proline was obtained in 69% (0.89 gm) yield as white flaky crystals.

EXAMPLE 11

4-Phenyl-1-[(phenylmethoxy)carbonyl]-3,4-dihydro-L-proline benzyl ester

Following the procedure as described in Example 3, except substituting the Example 7B proline compound for the Example 2 proline compound, the title compound is obtained.

EXAMPLE 12

(trans)-4-Phenyl-L-proline

The procedure as described in Example 4 was followed except that the Exaple 11 compound was used as the starting material. Thus, a solution of 2.0 g (0.0048 moles) of the dehydro proline in 20 ml THF was added to a solution of lithium (0.27 g, 0.0387 moles) in ammonia (150 ml) and THF (10 ml) at ∼−78° C. After the addition, the reaction was stirred for 20 minutes at −78° C., quenched with 1.0 g of ammonium chloride and worked up using the procedure as in Example 4 to obtain 0.43 g of title product (46%) as white crystals.

EXAMPLE 13

(trans)-4-Cyclohexyl-L-proline hydrochloride

A slurry of (trans)-4-phenyl-L-proline (50 g, 0.262 moles) and platinum oxide (10 g) in absolute ethanol (1200 ml) was treated with 5.62 N ethanolic HCl (46.5 ml, 0.261 moles) and shaken until all the solid had gone into solution. The solution was then purged with argon and hydrogenated on a Parr apparatus at 50 psi overnight. After this time, the untake of hydrogen had ceased and NMR indicated complete reduction. The reaction mixture was filtered through a pad of Cellite and concentrated in vacuo. The residue was triturated with diethylether and filtered to yield 60.0 g of (trans)-4-cyclohexyl-L-proline hydrochloride as snow white crystals, m.p. 170°–171° C.

EXAMPLE 14

(trans)-4-Cyclohexyl-L-proline

A solution of 2.0 g (0.0062 moles) of dehydro proline (prepared as described in Example 3) in 10 ml THF was added to a solution of lithium (0.65 g, 0.093 moles) in ammonia (150 ml) at ∼−78° C. After the addition, the reaction mixture was stirred for 20 minutes and then absolute ethanol (3.6 ml, 0.062 moles) was added to the reaction mixture. The reaction mixture was stirred at −33° C. for 6 hours and quenched with 2.0 g of ammonium chloride. Ammonia was evaporated and the residue was acidified to pH=1 using 5% HCl and extracted with ethyl acetate (2 x 100 ml). Palladium hydroxide on carbon (20%, 0.25 g) was added to the aqueous layer and hydrogen gas was bubbled through the solution at room temperature for about 3 hours. It was filtered through a celite pad and the filtrate was concentrated and pH was adjusted to 6.3 by adding 5% NaOH solution. The precipitated product was filtered the next day, and vacuum dried to obtain 0.52 g of trans-4-cyclohexyl-L-proline as white flaky solid.

What is claimed is:

1. A compound useful in preparing (cis)-4-hydroxy-4-phenyl proline derivatives or (trans)-4-phenyl proline prepared by the process which comprises reacting cerium trichloride and phenyllithium at a temperature within the range of from about −90° C. to about −50° C., for a period of from about 0.1 to about 1 hour, wherein the cerium trichloride is employed in a molar ratio to the phenyllithium of within the range of from about 0.2:1 to about 0.35:1.

2. A process for preparing a compound useful in preparing (cis)-4-hydroxy-4-phenyl proline derivatives or (trans)-4-phenyl proline, which comprises reacting cerium trichloride and phenyllithium at a temperature within the range of from about −90° C. to about −50° C., for a period of from about 0.1 to about 1 hour, wherein the cerium trichloride is employed in a molar ratio to the phenyllithium of within the range of from about 0.2:1 to about 0.35:1.

3. The process as defined in claim 2 wherein the cerium trichloride is employed in a molar ratio to the phenyllithium of within the range of from about 0.25:1 to about 0.35:1.

4. The process as defined in claim 2 wherein the reaction of cerium trichloride and phenyllithium is carried out at a temperature within the range of from about −80° C. to about −50° C.

5. The process as defined in claim 4 wherein the reaction is carried out for a period of from about 0.2 to about 1.hour.

6. The process as defined n claim 4 wherein the reaction is carried out in the presence of an inert organic solvent.

* * * * *